United States Patent
Oren et al.

(10) Patent No.: US 7,605,207 B2
(45) Date of Patent: Oct. 20, 2009

(54) FLAME RETARDANT BROMOBENZYL SYSTEMS

(75) Inventors: Jakob Oren, Nesher (IL); Nasif Yassin, Tamra (IL); Joseph Zilberman, Haifa (IL); Dorit Canfi, Haifa (IL); Ron Frim, Haifa (IL); Dov Beruben, Beer Sheva (IL)

(73) Assignee: Bromine Compounds Ltd., Beer Sheva (IL)

( * ) Notice: Subject to any disclaimer, the term of this patent is extended or adjusted under 35 U.S.C. 154(b) by 0 days.

(21) Appl. No.: 12/093,566

(22) PCT Filed: Nov. 16, 2006

(86) PCT No.: PCT/IL2006/001327

§ 371 (c)(1),
(2), (4) Date: May 29, 2008

(87) PCT Pub. No.: WO2007/057900

PCT Pub. Date: May 24, 2007

(65) Prior Publication Data

US 2008/0281024 A1    Nov. 13, 2008

(30) Foreign Application Priority Data

Nov. 21, 2005  (IL) .................................... 172077

(51) Int. Cl.
*C08K 5/03* (2006.01)

(52) U.S. Cl. .................. 524/469; 524/464; 570/182; 570/184; 570/185; 570/199; 570/252; 570/254

(58) Field of Classification Search .............. 524/464, 524/469; 570/182, 184, 185, 199, 252, 254
See application file for complete search history.

(56) References Cited

U.S. PATENT DOCUMENTS

| 5,639,799 A | 6/1997 | Books et al. |
| 5,717,001 A | 2/1998 | Books et al. |
| 6,579,911 B1 | 6/2003 | Vo et al. |
| 2005/0043464 A1 | 2/2005 | Pederson |

FOREIGN PATENT DOCUMENTS

| GB | 1364397 A | 8/1974 |
| WO | WO 91/19758 A1 | 12/1991 |

OTHER PUBLICATIONS

PCT/IL06/01327 Search Report dated Jun. 19, 2008.

*Primary Examiner*—Peter Szekely
(74) *Attorney, Agent, or Firm*—Roach Brown McCarthy & Gruber, P.C.; Kevin D. McCarthy

(57) ABSTRACT

Polybrominated bisaryl compounds containing bromomethyl or bromomethylene groups are provided, as well as flame-proof polymeric formulations comprising the compounds. The novel compounds exhibit a good thermal stability, and are particularly suitable for flame-retarding polystyrene thermoplastic foams. A process for making the polybrominated bisaryl compounds is also provided.

18 Claims, No Drawings

FLAME RETARDANT BROMOBENZYL SYSTEMS

FIELD OF THE INVENTION

The present invention relates to imparting flame-retardant properties to styrene polymers, particularly to polystyrene thermoplastic foams, via the incorporation of novel polybrominated bisaryl compounds containing bromomethyl or bromomethylene groups.

BACKGROUND OF THE INVENTION

Foamed polystyrenes are employed to an increasing extent in many fields, above all in the building, construction and packaging industries. In many cases it is desired to decrease the flammability of such products by incorporating a flame retardant into them.

It is common to use brominated aliphatics in the foamed polystyrene industry, with hexabromocyclododecane (HBCD) being the most commonly used flame retardant in foamed styrene polymers. The vapor phase mode of action of brominated organic flame retardants relies to a great extent on their thermal stability in relation to that of the polymer. It is desirable to have a flame retardant compound whose thermal stability is close to that of the polymer. This mainly explains the high efficiency of the brominated aliphatics, and among them HBCD, in imparting flame retardant properties to the cellular and foamed polymer materials.

The process for the production of foamed polystyrene, especially extruded polystyrene (XPS), is very sensitive to the quality of the HBCD due to the relatively low thermal stability of HBCD and some of the typical impurities in it. It is extremely important that the flame retardant chosen for foamed polystyrene has good thermal stability. Hydrogen bromide formed as a result of the thermal decomposition of HBCD during the processing/foaming of polystyrene will adversely affect the physical properties of the foamed polymer product. In addition, the HBr formed may cause corrosion of the metal equipment with which the hot blend comes into contact during the process. Furthermore, the industry aims at increasing the operating temperatures, for higher productivity of the process. In order to suppress such undesirable, early, decomposition and to optimize the performance, HBCD usually needs to be stabilized by the addition of a variety of metal-organic and epoxy compounds, in order to allow the processing of HBCD at higher temperatures and for a longer period.

In view of the above, it can be seen that a need exists for bromine-containing compounds which would be efficient fire retardants for foamed polystyrenes while being more thermally stable than HBCD and other known aliphatic bromine-containing compounds both during the production of the foamed polystyrenes and their processing and scrap recycling.

A Dow patent document, WO 91/19758, describes the limited fire retardancy of HBCD, and discloses the use of a mixture of aliphatic bromine compounds, especially HBCD and aromatic bromine compounds such as decabromodiphenyl ether, as flame retardants for polystyrene foams. Another Dow patent, U.S. Pat. No. 6,579,911, discloses an application of HBCD, phosphorous compounds and flow promoters, to improve the flame retardant efficiency of HBCD. The patent emphasizes that, typically, only brominated aliphatic compounds are utilized with styrene-based foams, with HBCD being the most common.

US 2005/0043464 discloses topical application of brominated aromatic compounds, used as additives to beads of polystyrene in a process for making expanded polystyrene molded patterns in lost foam aluminum castings. The brominated compounds accelerate depolymerization of the polystyrene by the liberation of bromine radicals, which reduce the viscosity of the liquid polystyrene.

U.S. Pat. Nos. 5,639,799 and 5,717,001 describe methods of improving the thermal stability of HBCD for application in styrenic polymer foam compositions.

It is, therefore, an object of the present invention to provide novel bromine-containing fire retardants, which have both excellent thermal stability and good fire-retardancy properties, particularly when incorporated in foamed polystyrene.

It is another object of the present invention to provide such novel fire retardants of suitable thermal stability against dehydrobromination both during the production of the foamed polystyrenes and their processing.

It is yet another object of the present invention to provide a flameproof foamed polystyrene formulation, which contains such bromine-containing fire retardants.

It is yet another object of the present invention to provide use of the novel compounds of the invention and mixtures thereof, as flame-retarding agents in polymeric materials, particularly in foamed polystyrenes.

The present invention provides novel polybrominated bisaryl compounds containing bromomethyl or bromomethylene groups which are capable of imparting highly satisfactory flame-retarding qualities to foamed polystyrenes, while being thermally stable against dehydrobromination both during the production of the foamed polystyrenes and their processing. The invention further provides foamed polystyrene compositions containing the said novel polybrominated bisaryl bromomethyl/bromomethylene compounds and mixtures thereof that exhibit excellent fire retardancy.

Other objects and advantages of the invention will become apparent as the description proceeds.

SUMMARY OF THE INVENTION

The present invention provides novel polybrominated bisaryl compounds comprising bromomethyl or bromomethylene groups according to the following formula (I):

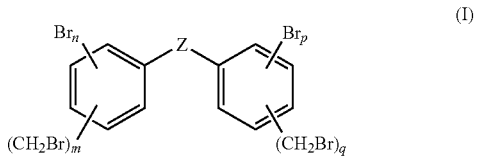

wherein a) Z is a bond, —O—, —CH$_2$—, —CH(CH$_3$)—, —OCH$_2$CH$_2$O—, m=1-4, n=1-4, p=1-4, and q=1-4; or b) Z is —CH(Br)—CH(Br)—, n=1-4, p=1-4, m=0, and q=0.

Preferred compounds according to formula (I) of the present invention have a formula selected from the following group consisting of formulae A to F:

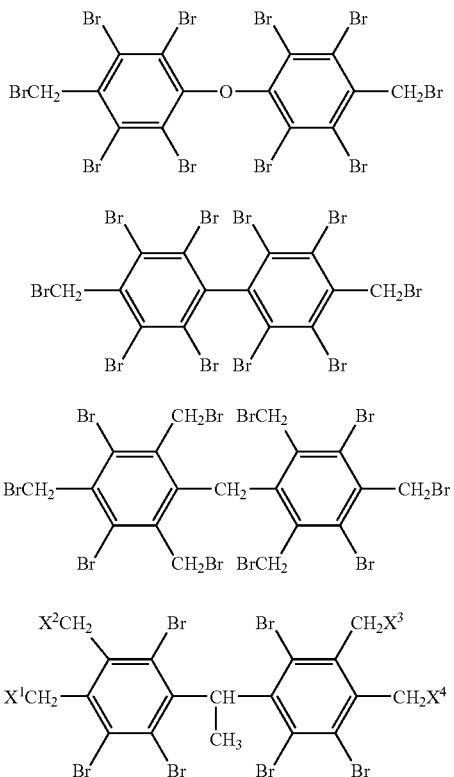

wherein $X^1$, $X^2$, $X^3$, and $X^4$ are independently H or Br wherein at least one of them is Br;

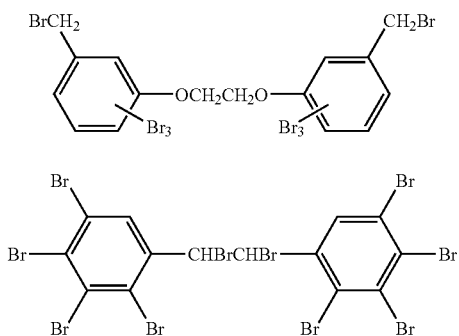

The present invention also provides processes for the preparation of the said novel compounds by bromination of the corresponding bisaryl compounds.

The polybrominated bisaryl compounds of this invention possess excellent thermal stability and are useful as flame retardants in styrene-containing polymers, preferably in polystyrene, and most preferably in foamed polystyrene. The present invention further provides fire retarded foamed polystyrene compositions comprising said novel polybrominated bisaryl compounds, and mixtures thereof, as flame retarding agents. All the above and other characteristics and advantages of the invention will be better understood through the following illustrative and non-limitative detailed description of the preferred embodiments thereof.

DETAILED DESCRIPTION OF PREFERRED EMBODIMENTS

It is an object of the present invention to provide a group of novel polybrominated bisaryl compounds containing bromomethyl or bromoethylene groups. The preparation of the novel compounds of formulae A to F of the invention comprises aromatic ring-bromination, and, except for compound of formula F, radical bromination to produce bromomethyl groups. The bromomethyl groups in the compound of formula F result from a bromine addition reaction to a double bond of stilbene.

Aromatic Ring-Bromination

The aromatic bromination is carried out in a suitable organic solvent. or in bromine as a solvent. Halogenated lower alkanes of 1-6 carbon atoms free of carbon to carbon unsaturation are suitable for this purpose. Specific useful solvents include carbon tetrachloride, chloroform, dichloroethane, tetrachloroethane, methylene chloride, dibromomethane and bromochloromethane, or mixtures thereof. Preferably, the solvent is substantially anhydrous. Water destroys the catalyst and causes the reaction to proceed at a slower rate. As used here, the term "solvent" includes one of the reactants itself which has the described requirements of the solvent. For example, bromine in excess can itself serve as the solvent.

The aromatic bromination is performed in the presence of a Lewis acid catalyst, and optionally for some of the bisaryl substrates (compounds of formulae C and D) no catalyst is needed to achieve the necessary degree of bromination.

The most desirable Lewis acid catalysts are those metal halides capable of effecting a Friedel-Crafts reaction. Of these, the preferred ones are the bromides and chlorides of aluminium and antimony. However, metals such as Fe and Sn, or metal oxides, for example antimony oxide, are not excluded from the scope of the present invention, and may also be used as catalysts according to the present invention. An amount of the catalyst is used which can be readily determined by routine experiment. In general, the amount of catalyst used may range from 5% to 25%, and preferably from 10% to 22%, by weight of the bisaryl substrate.

Any stoichiometric excess of bromine over the bisaryl substrate is effective to encourage complete aromatic ring-bromination within a reasonable period of time. Generally, the excess of bromine to the bisaryl compound to be fully brominated is at least 5% molar. As said above, bromine can optionally be used as the solvent. The rate of adding the bromine is not critical as long as a stoichiometric excess is present at least at the end of the reaction to encourage as complete a bromination as possible. As an example, a stoichiometric excess of bromine can be added to the bisaryl substrate over a period of time from about 30 min to 3 hours.

Bromine chloride, by which a mixture of bromine and chlorine is meant, may also be used as a brominating agent for the aromatic bromination in the process of the present invention. Bromine and chlorine are generally used in a molar ratio of from (0.7-1.3):1, and preferably bromine and chlorine are used in about a 1:1 molar ratio. Generally, the excess of bromine chloride to the bisaryl substrate is at least 5% molar.

The temperature of the process is preferably from 0° C. up to about 80° C. The reaction is usually completed within about two to ten hours, depending on the conditions and reactants.

The final reaction mixture is treated by adding successively water and a reducing agent such as sodium bisulfite, sodium sulfite or hydrazine. The water destroys and removes the catalyst. The reducing agent neutralizes the excess bromine (in the case of the compound of formula F after the distillation of most of the bromine).

In one mode suitable for the purpose of the present invention, successive aromatic and benzylic brominations of the brominated product are carried out by isolating the aromatic brominated product prior to the benzylic bromination In another suitable mode, both aromatic and benzylic bromination are carried out as a one-pot two-stage process without isolating the intermediate polybrominated bisaryl compound.

Benzylic Bromination

The second chemical stage (for compounds of formulae A to E) is a selective monobromination of the methyl group (also known as benzylic bromination) in the intermediate products isolated after the aromatic bromination. This is achieved by a radical process, using some source of radical initiator to convert the bromine molecule into reactive radicals which attack the methyl group to form the bromomethyl functionality. The choice of radical source is rather limited while the influence of the initiator on the final purity of the product is significant One of the most suitable radical initiators for this purpose is 2,2'-azobisisobutyronitrile (AIBN). The decomposition of AIBN is essential for the benzylic bromination to proceed since the radicals formed by the decomposition of the AIBN initiate the formation of bromine radicals which are the active brominating species in this type of reaction. It is highly recommended that such reactions be performed at temperatures that will ensure a high selectivity together with a reasonable reaction time. At a too low temperature the formation of the radicals will be slowed down so that no effective reaction will occur. The temperature of the process is preferably from 60° C. up to 80° C., with temperatures from about 69° C. to about 75° C. being most preferred. Photochemical reaction can also be a source for Br radicals.

The benzylic bromination is preferably carried out in a halogenated organic solvent which boils in this range of temperatures. A mixture of dichloromethane, bromochloromethane and dibromomethane in a ratio of 10:20:70 wt. meeting such a requirement is the most preferred. An effective amount of the AIBN employed in the benzylic bromination is in a range of 5 to 50% by weight, and preferably 10 to 40% by weight to the amount of the ring-brominated intermediate substrate.

The presence of an appropriate amount of water is essential for a high benzylic bromination efficiency. A stoichiometric excess of bromine in a range of 1.1 mol to 2 mol per methyl group, and preferably in a range of 1.2 to 1.8 mol bromine per methyl group, in the ring-brominated intermediates is effective in achieving complete benzylic bromination within a reasonable period of time.

The final reaction mixture is treated by the addition of a reducing agent such as sodium bisulfite, sodium sulfite or hydrazine to neutralize the excess bromine.

The following examples illustrate specific embodiments of both the preparation of the novel polybrominated bisaryl compounds of the invention and the utility of these compounds as flame retardants in foamed polystyrenes. The following examples should not be construed as limiting the scope of the invention.

EXAMPLE 1

Preparation of the Compound of Formula A

A 1 liter jacketed reactor, equipped with a mechanical stirrer, a thermocouple and a reflux condenser, was charged with a solvent mixture of dichloromethane, bromochloromethane and dibromomethane (20:40:40 wt., 500 g), $AlCl_3$ (5 g) and p-tolyl ether (50 g). The temperature was set at 20° C., then bromine (350 g) was fed in via a peristaltic pump at a rate of 3 g/min. A post-reaction of 2.5 hours at reflux brought the reaction to completion (confirmed by GC analysis).

Work-up and isolation of the crude octabromodimethyldiphenyl ether was performed by adding water (100 g) and aq. 17% hydrazine (30 g) to the reaction mixture for catalyst destruction and reduction of excess bromine. The aqueous layer was separated. The organic slurry was mixed with water (100 g), filtered, and washed with solvent mixture (57 g) and water (100 g).

After vacuum drying there was obtained 196 g of octabromo-dimethyldiphenyl ether (93% of the theoretical, based on p-tolyl ether).

A mixture of bromochloromethane and dibromomethane (20:80 wt., 500 g), octabromodimethyldiphenyl ether (185 g), bromine (107 g) and water (107 g) were introduced into the reactor. The mixture was heated to 69° C., and azobis-isobutyronitrile (AIBN) was added in small portions (8×2 g) over 5 hours.

The reaction mixture was cooled to 40° C. and the excess bromine was neutralized with aq. 17% hydrazine (25 g). The aqueous phase was separated. The organic slurry was mixed with water (120 g), filtered, and washed with solvent mixture (50 g) and water (125 g). After vacuum drying there was obtained 206 g (94% of the theoretical, based on octabromodimethyldiphenyl ether) of pure 1,1'-oxybis(4-bromomethyl-2,3,5,6-tetrabromo)benzene (compound A, confirmed by HPLC/MS, $H^1$-NMR) in the form of a white powder, melting point 266-268° C., % Br calculated: 81.0%, found: 81.7% benzylic Br calculated: 16.2%, found 16.4%. Differential scanning calorimetry (DSC) analysis showed the purity to be 99%. Thermogravimetric analysis (TGA): 5 and 10% weight loss at 346° C. and 359° C., respectively.

EXAMPLE 2

Preparation of the Compound of Formula B

A 0.5 liter jacketed reactor, equipped with a mechanical stirrer, a thermocouple and a reflux condenser, was charged with a solvent mixture of dichloromethane, bromochloromethane and dibromomethane (20:40:40 wt., 150 g), $AlCl_3$ (2 g) and 4,4'-dimethylbiphenyl (9.1 g). The temperature was set at 25° C., and then bromine (70 g) was fed in over a period of 1.5 hour. A post-reaction of four hours at reflux brought the reaction to completion (confirmed by GC analysis).

Work-up and isolation of the crude octabromodimethylbiphenyl was performed by adding water (75 g) and aq. 17% hydrazine (8 g) to the reaction mixture for catalyst destruction and reduction of excess bromine. The aqueous layer was separated. The organic slurry was mixed with water (50 g), filtered, and washed with solvent mixture (20 g) and water (70 g).

After vacuum drying there was obtained 31.5 g of octabromodimethylbiphenyl (77% of the theoretical, based on 4,4'-dimethylbiphenyl).

A mixture of bromochloromethane and dibromomethane (15:85 wt., 140 g), octabromodimethylbiphenyl (26 g), bromine (18 g) and water (25 g) were introduced into the reactor. The mixture was heated to 72-75° C., and AIBN was added in small portions (5×2 g) over 5 hours.

The reaction mixture was cooled to 40° C. and the excess bromine was neutralized with aq. 17% hydrazine (4 g). The aqueous phase was separated. The organic slurry was mixed with water (50 g), filtered, and washed with solvent mixture (10 g) and water (25 g). After vacuum drying there was obtained 22 g (71% of the theoretical, based on octabromodimethylbiphenyl) of pure 4,4'-bisbromomethyl-octabromo-biphenyl (compound B, confirmed by HPLC/MS, $^1$H-NMR) in the form of a white powder, melting point 320-322° C., % Br calculated: 82.3%, found: 82.6% benzylic Br calculated: 16.5%, found 16.7%. TGA: 5 and 10% weight loss at 325 and 339° C.

EXAMPLE 3

Preparation of the Compound of Formula C

A 0.5 liter jacketed reactor, equipped with a mechanical stirrer, a thermocouple and a reflux condenser, was charged with a solvent mixture of dichloromethane, bromochloromethane and dibromomethane (20:40:40 wt., 100 g) and bromine (145 g). The temperature was set at 25° C., then a solution of bismesityl methane (38 g) in solvent mixture (200 g) was fed in over a period of 1.5 hours. A post-reaction of two hours at 25° C. brought the reaction to completion (confirmed by GC analysis).

Work-up and isolation of the crude bis(3,5-dibromo-2,4,6-trimethyl)methane was performed by adding water (100 g) and aq. 37% NaHSO$_3$ (110 g) to the reaction mixture for reduction of excess bromine. The aqueous layer was separated. The organic slurry was filtered, and washed with solvent mixture (40 g) and water (55 g).

After vacuum drying there was obtained 72 g of bis(3,5-dibromo-2,4,6-trimethyl)methane (84% of the theoretical, based on bismesityl methane), melting point 284-287° C.

A mixture of bromochloromethane and dibromomethane (25:75 wt., 80 g), bis (3,5-dibromo-2,4,6-trimethyl)methane (17 g), bromine (40 g) and water (40 g) were introduced into the reactor. The mixture was heated to 74-76° C., and AIBN was added in small portions (6×0.5 g) over 7 hours.

The reaction mixture was cooled to 40° C. and the excess bromine was neutralized with aq. 37% NaHSO$_3$ (8 g). The aqueous phase was separated. The organic solution was washed with water (40 g), followed by phase separation and stripping of about half of the solvent mixture. The precipitate was filtered, and washed with dichloromethane (10 g) and water (30 g). After vacuum drying there was obtained 20 g (64% of the theoretical, based on bis((3,5-dibromo-2,4,6-trimethyl)methane), of bis(3,5-dibromo-2,4,6-tribromomethylphenyl)methane (compound C, confirmed by HPLC/MS, $^1$H-NMR) in the form of a white powder, melting point 214-216° C., % Br calculated: 76.8%, found: 74.8%, benzylic Br calculated: 46.1%, found 44.8%. TGA: 5 and 10% weight loss at 271° C. and 284° C.

EXAMPLE 4

Preparation of the Compounds of Formula D

A 1 liter jacketed reactor, equipped with a mechanical stirrer, a thermocouple, and a reflux condenser, was charged with a solvent mixture of dichloromethane, bromochloromethane and dibromomethane (20:40:40 wt., 350 g) and bromine (350 g). The temperature was set at 24° C., then 1,1-bis(3,4-dimethylphenyl)ethane (83 g) was fed in over a period of 2 hours. A post-reaction of three hours at 40° C. brought the reaction to completion (confirmed by GC analysis).

Work-up and isolation of the mixture of 1-(dibromodimethyl-phenyl)-1-(dibromodimethyl-phenyl)ethanes was performed by adding water (50 g) and aq. 37% sodium bisulfite (208 g) to the reaction mixture for reduction of excess bromine. The aqueous layer was separated. The organic slurry was mixed with solvent mixture, filtered, and washed with solvent mixture and water. After vacuum drying there was obtained 178 g (92% of the theoretical, based on 1,1-bis(3,4-dimethylphenyl)ethane) of an mixture of 1-(dibromodimethylphenyl)-1-(dibromodimethylphenyl)ethanes, melting point 222-224° C.

A mixture of bromochloromethane and dibromomethane (25:75 wt., 150 g), mixture of 1-(dibromodimethylphenyl)-1-(dibromodimethylphenyl)ethanes (55 g), bromine (80 g) and water (80 g) were introduced into the reactor. The mixture was heated to 74-76° C., and AIBN was added in small portions (6×1 g) over 5 hours. The reaction mixture was cooled to 40° C. and the excess bromine was neutralized with aq. 37% sodium bisulfite (8 g). The aqueous phase was separated. The organic phase was washed with water (60 g), followed by partial evaporation of the solvent. After cooling to 5° C. the precipitate formed was filtered, and washed with dichloromethane (33 g) and water (50 g). After vacuum drying there was obtained 18 g (about 20% of the theoretical, based on 1,1-bis((dibromodimethylphenyl)ethane), of a mixture of brominated (at three methyl groups on the benzene rings) 1-(tribromobromomethyl methylphenyl)-1-(tribromodimethylphenyl)ethanes (compounds of formula D, confirmed by HPLC/MS) in the form of a white powder, melting point 191-195° C., % Br calculated: 77.8%, found: 78.1%, benzylic Br calculated: 31.1%, found 24.6%. TGA: 5 and 10% weight loss at 274 and 290° C.

EXAMPLE 5

Preparation of the Compounds of Formula E

A 2 liter reactor, equipped with a mechanical stirrer, a thermocouple and a reflux condenser, was charged with dichloroethane (1120 g), bis(3-methylphenoxy)ethane (40 g) and antimony oxide Sb$_2$O$_3$ (6.6 g). Bromine (316.4 g) was fed in via a peristaltic pump over 1 hour at room temperature. After the addition of half the amount of bromine, the reaction mixture was heated to 40° C. After the bromine addition was completed the reaction mixture was heated at 75-77° C. over a period of 8 hours. The reaction mixture was cooled to room temperature, water (100 g) was added, then aq. 37% sodium bisulfite was added for catalyst destruction and reduction of excess bromine. The solid was filtered and washed with dichloroethane, then with 5% sodium bicarbonate solution and water. After vacuum drying there was obtained 102.7 g of 1-(tribromo-3-methylphenoxy)-2-(tribromo-3-methylphenoxy)ethanes (87% of the theoretical, based on bis(3-methylphenoxy)ethane), melting point 242-244° C. GC analysis showed the purity to be above 98% (area %).

A mixture of dichloro-, bromochloro- and dibromomethane (10:20:70 wt., 2100 g), 1-(tribromo-3-methylphenoxy)-2-(tribromo-3-methyl-phenoxy)-ethanes (96 g), bromine (60 g) and water (100 g) were introduced into the reactor. The mixture was heated to 70-73° C. AIBN (5 g) was added to the mixture in five portions, 1 hour between each portion. The reaction mixture was cooled to 25° C. The bromine excess was reduced with aq. 37% sodium bisulfite solution. The organic mixture was washed with water and neutralized with aq. 5% sodium bicarbonate solution. The precipitate was filtered and washed with dichloromethane and water. After vacuum drying there was obtained 111.6 g (95% of the theoretical, based on 1-(tribromo-3-methylphenoxy)-2-(tribromo-3-methyl-phenoxy) of pure 1-(tribromo-3-bromomethylphenoxy)-2-(tribromo-3-bromomethylphenoxy)ethanes (compounds of formula E, confirmed by HPLC/MS, ¹H-NMR) in the form of a white powder, melting point 238-240° C., % Br calculated: 73.2, found: 73.1, % benzylic Br calculated: 18.3, found 18.0. HPLC analysis showed the purity to be above 99.5% (area %). NMR suggested that most of the material is represented by a symmetric formula of bis(tribromo-3-bromomethylphenoxy)ethane. TGA: 5 and 10% weight loss at 294° C. and 300° C.

EXAMPLE 6

Preparation of the Compound of Formula F

Two-Step Process

A 1 liter jacketed reactor, equipped with a mechanical stirrer, a thermocouple and a reflux condenser, was charged with dichloromethane (520 g) and trans-stilbene (54 g), followed by the addition of bromine (50 g). After 1 h stirring at room temperature, 200 ml of water was introduced into the reactor and the excess bromine was neutralized with aq. 37% sodium bisulfite. The organic solvent was then distilled. The obtained slurry was filtered to give 98.2 g (96.3% of the theoretical, based on trans-stilbene) of 1,2-dibromo-1,2-diphenylethane as a pale yellow solid.

A 0.5 liter jacketed reactor equipped with a mechanical stirrer, a thermometer and a reflux condenser was charged with bromine (310 g), 1,2-dibromo-1,2-diphenylethane (20.4 g) and AlCl₃ (2 g). The reaction was slightly exothermic. The reaction mixture was stirred until no more HBr was evolved. Water (100 g) was added dropwise and the mixture was heated to 60° C. for the distillation of the major part of unreacted bromine. The obtained slurry was treated with aq. 37% sodium bisulfite, filtered and washed with water. The filtered powder was poured into xylene (200 ml) and aq. 37% sodium bisulfite (60 g) and heated to 70° C. for 4 h. After filtration, washing with water and vacuum drying, there was obtained 52 g (90% of the theoretical based on 1,2-dibromo-1,2-diphenylethane) of 1,2-dibromo-1,2-bis(2,3,4,5-tetrabromophenyl)ethane (compound of formula F, confirmed by, X-Ray) in the form of a white solid, melting point 282-283° C., % Br calculated: 82.2%, found: 80.5%. TGA: 5 and 10% weight loss at 291 and 295° C.

One-Step Process

A 0.5 liter jacketed reactor, equipped with a mechanical stirrer, a thermometer and a reflux condenser, was charged with bromine (750 g), trans-stilbene (21.6 g) and AlCl₃ (4.2 g). The reaction mixture was stirred until no more HBr evolved. Work-up and isolation of the product was performed as described for the two-step process. After vacuum drying there was obtained 107 g (92% of the theoretical, based on trans-stilbene) of 1,2-dibromo-1,2-bis(2,3,4,5-tetrabromophenyl)ethane (compound of formula F).

Besides the novel brominated flame-retarding agents of the present invention, the flame-retarding compositions, prepared according to the method of the present invention, may incorporate other additives as processing aids, synergists, and flow-promoters, aiding in imparting flame-retardant qualities to the host polymer material. Thus, U.S. Pat. No. 6,579,911 describes mixtures of polystyrenes, phosphorous compounds and flow promoters. Preferably, the synergist is an organophosphorous compound, including phosphates, phosphonates, phosphinates, phosphites and phosphine oxides. Particularly, such organophosphorous synergists may be of a monomeric, dimeric or oligomeric type, and may contain aromatic moieties.

Particularly suitable organophosphorous synergists having aromatic moieties include aromatic phosphate esters, represented by formula (II):

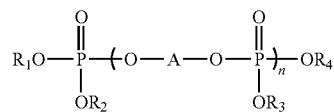

in which R₁, R₂, R₃, and R₄ are aryl groups, which may be the same or different, A is an arylene group, and 'n' is an integer from 0 to 5. The phosphate esters can be either triarylphosphates, where 'n' in the formula given above is 0, or monomeric bisphosphates, where 'n' in the formula is 1, or mixtures of said triaryl phosphates and monomeric bisphosphates with higher oligomers, where 'n' for each oligomer is an integer from 2 to 5 (said mixtures hereinafter indicated also as oligomeric phosphates).

The aryl group may be phenyl, cresyl, 2,6-xylenyl, and the like. The arylene group may be a group derived from a dihydric compound, for example, resorcinol, bisphenol-A, 4,4'-biphenol, and the like. Especially preferred arylphosphate esters for use herein include triphenyl phosphate (TPP) and phenylphosphate esters of 4,4'-biphenol. Preferably, the phosphorous synergists may consist of a single phosphorus-containing material or they may consist of a mixture of two or more different organic phosphorus-containing compounds, which may be suitable for obtaining the desired properties of the polystyrene foam.

The phosphorous synergist may typically, although non-limitatively, be present in amounts ranging from about 0.1% to about 10.0% by weight based on 100% of the styrene polymer. Most preferably, the amount of phosphorous synergist in the composition ranges from about 0.5% to about 2.0% by weight based on 100% of the styrene polymer. The flame-retarding composition, containing an organophosphorous flame-retardant as synergist, can be used either as a viscous liquid or more preferably as solid flakes (TPP) or as a preliminary melt mixed in the polystyrene polymer.

In another preferred embodiment of the present invention flow promoters are selected from dimethyldiphenylbutane, dicumyl peroxide or α,α'-bis-tert-butylperoxydiisopropylbenzene, and diethyldiphenylbutane, in typical amounts of between about 0.01% and about 0.2% by weight based on 100% of styrene polymer. More preferably, the amounts range from about 0.02% to about 0.1% by weight based on 100% of styrene polymer. An illustrative example of a flow-promoter is dicumyl (2,3-dimethyl-2,3-diphenylbutane).

Process Background and Experimental Conditions

Test Methods

It is well known that the performance of injection molded and compression molded flame retarded polystyrene measured by LOI and UL-94 can be taken as indicative of the performance of flame retardant additives in foamed polystyrene.

Therefore, injection molded and compression molded specimens were used to exemplify the efficiency of the novel polybrominated bisaryl compounds of the invention, as flame retardants in polystyrene. For this purpose injection molded or compression molded specimens were prepared and their flame retardancy measured by the methods detailed in Table 1.

TABLE 1

Test methods, Standard flammability test methods for compression molded and injection molded polystyrene

| PROPERTY | METHOD | APPARATUS |
|---|---|---|
| LOI (Limiting Oxygen Index) | ASTM D 2863-77. Measuring the minimum oxygen concentration to support candle-like combustion of plastics. | Stanton Redcroft FTA Flammability Unit. |
| Flammability | UL-94 Vertical burning test at 3.2 mm (Underwriter Laboratories) | Hood and burner as specified by UL |

Compounding

All the components (plastic pellets and powders) were weighed on Sartorius semi-analytical scale with subsequent manual mixing in a plastic bag. Formulations were compounded in a Berstorff twin-screw extruder Type ZE-25, L/D=32:1 fed from one feeder. The compounding conditions are presented in Table 2. The obtained strands were cooled in a water bath and then pelletized in the Pelletizer 750/3 ex. Accrapak Systems Limited. The obtained pellets were dried in a circulating air oven at 70° C. for two hours.

Injection Molding

The compounded pellets were molded using an Arburg-Allrounder machine model 320s/500-150. LOI and UL test specimens were molded using a no. S 22963 mold. The molding conditions are presented in Table 3.

TABLE 2

Regime of compounding in co-rotating twin-screw extruder ex Berstorff

| PARAMETER | UNITS | SET VALUES | ACTUAL VALUES |
|---|---|---|---|
| $T_1$ Feeding zone | ° C. | no heating | |
| $T_2$ | ° C. | 140 | 142 |
| $T_3$ | ° C. | 150 | 154 |
| $T_4$ | ° C. | 170 | 186 |
| $T_5$ | ° C. | 170 | 188 |
| $T_6$ | ° C. | 180 | 196 |
| $T_7$ vent | ° C. | 180 | 200 |
| $T_8$ | ° C. | 180 | 195 |
| $T_9$ nozzle | ° C. | 190 | 201 |
| Melt temperature | ° C. | | 203 |
| Screw speed | RPM | 375 | 375 |
| Ampere | A | | 11-12 |
| Feeding rate | kg/hour | 11.8 | 11.8 |

TABLE 3

Regime of injection molding

| PARAMETER | UNITS | VALUES |
|---|---|---|
| $T_1$ (Feeding zone) | ° C. | 160 |
| $T_2$ | ° C. | 180 |
| $T_3$ | ° C. | 180 |
| $T_4$ | ° C. | 180 |
| $T_5$ (nozzle) | ° C. | 180 |
| Mold temperature | ° C. | 40 |
| Injection pressure | bar | 900 |
| Holding pressure | bar | 700 |
| Back pressure | bar | 0 |
| Injection time | sec | 0.1 |
| Holding time | sec | 2 |
| Cooling time | sec | 10 |
| Mold closing force | kN | 131 |
| Filling volume (portion) | cc | 37 |
| Injection speed | cc/sec | 20 |

Compression Molding

All the components (plastic pellets and powders) were weighed on Sartorius semi-analytical scale with subsequent manual mixing. 70 gr of the mixture was compounded in a Brabender Plasticorder cell at 200° C. for 8 min and air cooled to 160° C. The compounding speed was 40 RPM.

Test plates of 127×6.5×3.2 mm were prepared by pressing the compounded mixture in a press type Polystat ex. Schuabenthan at the following setting: Press conditions: Temperature 180° C., first pressure 1 min, 0 bar, second pressure 1 min, 100 bar.

The pressed plates were cooled to 100° C. with running water and the samples were removed from the press. The plates were cut to LOI test specimens 6.5×127×3.2 mm. The test specimens were conditioned for 48 hours at ambient conditions before flammability tests.

Materials

Polystyrene used in the following examples was commercial polystyrene type 637 (ex Dow). Triphenyl phosphate, Reomol (ex Ciba Geigy) was used as a commercial example of the phosphate ester.

The flow promoter used was commercial Interox C-C DFB Peroxide Chemie; 2,3-dimethyl-2,3-diphenyl butane, also referred to as dicumyl.

Flame retardants of the present invention—novel brominated bisaryl compounds containing bromomethyl/bromomethylene groups—were selected from the group consisting of the compound of formula A, the compound of formula B, the compound of formula C, a compound of formula D or a mixture of compounds of formula D, a compound of formula E or a mixture of compounds of formula E, and the compound of formula F, which formulae A to F are described above.

The aforesaid and other characteristics and advantages of the invention will be better understood through the description of the following illustrative and non-limitative examples demonstrating the utility of the polybrominated bisaryl compounds of the invention as flame retardants in foamed polystyrenes.

EXAMPLES 7-13

Compression Molding

Polystyrene compression molding specimens 7-13, the compositions of which are detailed in Table 4, were compounded and molded substantially according to the procedures described above. Flammability testing of compression molded formulations 7-13 was conducted under standard LOI (Limiting Oxygen Index) testing, to which reference is made in Table 1.

Table 4 details the formulations, differing in the brominated bisaryl compound of the invention employed as flame retardant, with one formulation containing HBCD for reference. The flammability results of these compression-molded flame-retarded polystyrene specimens, measured according to the LOI standard procedure, are summarized in Table 4. The results clearly demonstrate that compression molded specimens can be used for evaluating the flame retardant performance of the products of the invention. Polybrominated bisaryl compounds containing bromomethyl groups pass the required levels.

TABLE 4

Composition and flammability of compression molded FR-PS test pieces

| Example No. | Br-FR type | % Br-FR | % Br in formulation (calculated) | LOI | Transparency |
|---|---|---|---|---|---|
| 7 | HBCD | 2.74 | 2.0 | 23.5 | Yes |
| 8 | Compound A | 2.5 | 2.0 | 23.3 | Yes |
| 9 | Compound B | 2.4 | 2.0 | 22.7 | Yes |
| 10 | Compound C | 2.7 | 2.0 | 24.6 | Yes |
| 11 | Compounds D | 2.6 | 2.0 | 25.7 | Yes |
| 12 | Compounds E | 2.7 | 2.0 | 24.3 | Yes |
| 13 | Compound F | 2.5 | 2.0 | 24.7 | Yes |

Table 4 shows that the efficiency of different polybrominated bisaryl compounds of the present invention as flame retardants for polystyrene is satisfactory, all behave in a similar way and are as efficient as HBCD. All the compression molded FR test pieces had good transparency. This indicates that the compounds of the invention are well compatible with the polystyrene.

EXAMPLES 14-19

Injection Molding

Polystyrene injection molding specimens 14-19, the compositions of which are detailed in Table 5, were compounded and injection molded substantially according to the compounding and injection molding procedures described above. Their regimes are detailed in Tables 2 and 3, respectively.

The flammability testing of injection molded formulations 14-19 described in Table 5, was conducted under the standard LOI (Limiting Oxygen Index) and UL 94 tests, to which reference is made in Table 1.

Table 5 details the different formulation components used for injection-molded specimens 14-19. The formulations contain polybrominated stilbene (compound of formula F) in different relative amounts, with or without the addition of a phosphorus-containing flame retardant synergist and dicumyl flow-promoter. One formulation contains HBCD for reference. The flammability results of these injection-molded flame-retarded polystyrene specimens, measured according to LOI and UL-94 standard procedures, are summarized in Table 5.

As mentioned above, injection-molded specimens can be used for evaluating the flame retardant performance of flame retardant products. According to the results in Table 5, polybrominated bisaryl compound F of the invention has an LOI value higher than that for HBCD. The data in Table 5 clearly demonstrates the advantage of employing synergists in the formulations. In all such formulations, the LOI is higher than in formulations that did not contain synergists.

TABLE 5

Composition and flammability of injection molded FR-PS test pieces

| Exp. No. | Br-FR type | % Br-FR | % Br in formulation (calculated) | P-FR (% P-FR) | % P in formulation (calculated) | % Interox CC DFB in formulation | LOI | UL-94 at 3.2 mm | Transparency |
|---|---|---|---|---|---|---|---|---|---|
| 14 | HBCD | 2.7 | 2 | — | — | — | 23.1 | V-2 | Yes |
| 15 | Comp. F | 2.9 | 2.0 | — | — | — | 25.0 | V-2 | Partial |
| 16 | Comp. F | 2.1 | 1.5 | — | — | — | 24.3 | V-2 | Yes |
| 17 | Comp. F | 1.4 | 1.0 | — | — | — | 22.3 | V-2 | Yes |
| 18 | Comp. F | 2.1 | 1.5 | TPP (1%) | 0.095 | 0.1 | 27.5 | V-2 | Yes |
| 19 | Comp. F | 2.1 | 1.5 | TPP (3%) | 0.29 | 0.4 | 29.1 | V-2 | Yes |

*TPP—Triphenyl phosphate

The invention claimed is:

1. Polybrominated bisaryl compounds containing bromomethyl/bromomethylene groups according to the following formula (I):

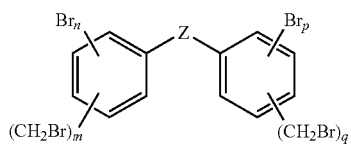

wherein
a) Z is a bond, —O—, —CH$_2$—, —CH(CH$_3$)—, —OCH$_2$CH$_2$O—, n=1-4, p=1-4, m=1-4, and q=1-4; or
b) Z is —CH(Br)—CH(Br)—, n=1-4, p=1-4, m=0, and q=0.

2. Polybrominated bisaryl compounds according to claim 1 having a formula selected from the group consisting of following formulae A to F:

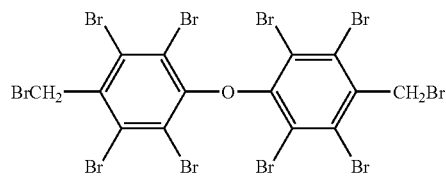

A.

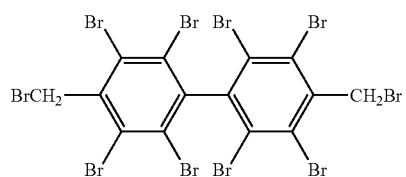

B.

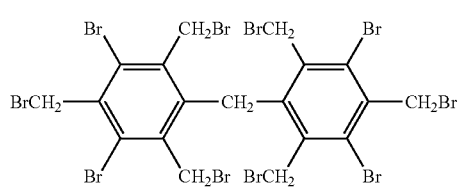

C.

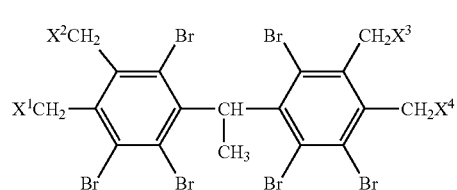

D.

wherein X$^1$, X$^2$, X$^3$, and X$^4$ are independently selected from H and Br wherein at least one of them is Br;

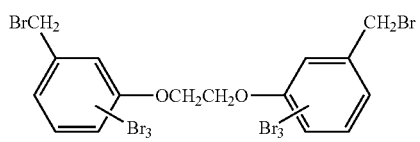

E.

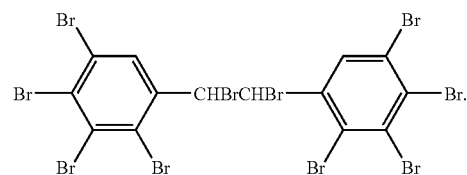

F.

3. A flameproof formulation comprising a polymeric material and at least one of the polybrominated bisaryl compounds containing bromomethyl/bromomethylene groups according to formula (I):

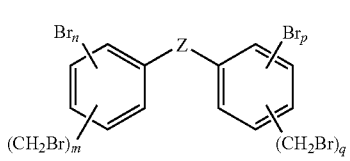

(I)

wherein
a) z is a bond, —O—, —CH$_2$—, —CH(CH$_3$)—, —OCH$_2$CH$_2$O—, n=1-4, p=1-4, m=1-4, and q=1-4; or
b) Z is —CH(Br)—CH(Br)—, n=1-4, p=1-4, m=0, and q=0.

4. A flameproof formulation according to claim 3, wherein said polybrominated bisaryl compounds have a formula selected from formulae A to F:

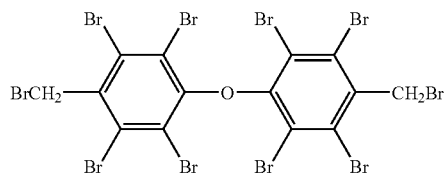

A.

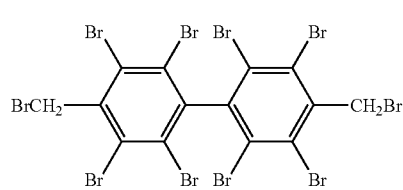

B.

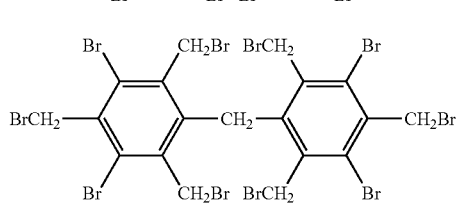

C.

-continued

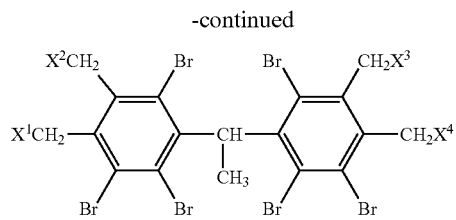
D.

wherein $X^1$, $X^2$, $X^3$, and $X^4$ are independently selected from H and Br wherein at least one of them is Br;

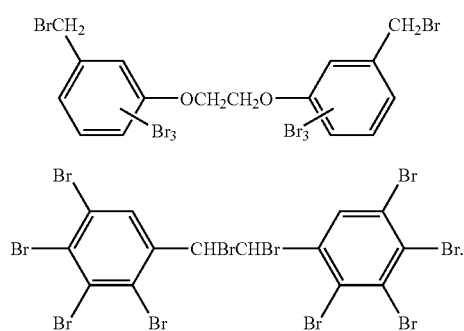
E.

F.

5. A flameproof formulation according to claim 3, wherein said polymeric material is selected from the group consisting of a styrene-containing polymer, polystyrene, and foamed polystyrene.

6. A flameproof formulation according to claim 5, wherein said polystyrene is rated V-2 under UL-94 standard.

7. A flameproof formulation according to claim 3, further comprising a synergist, said synergist being selected from the group consisting of an organophosphorous compound, a flow-promoter or a combination thereof.

8. A flameproof formulation according to claim 7, wherein the organophosphorous compound is present in an amount of from about 0.5% to about 10% by weight, based on 100% of polymeric material.

9. A flameproof formulation according to claim 7, wherein the organophosphorous compound is triphenyl phosphate.

10. A flameproof formulation according to claim 7, wherein the flow promoter is selected from the group consisting of dimethyldiphenylbutane, dicumyl peroxide, or α,α'-bis-tert-butylperoxydiisopropylbenzene, diethyldiphenylbutane, and 2,3-dimethyl-2,3-diphenylbutane.

11. A flameproof formulation according to claim 10, wherein the flow promoter is present in an amount of from about 0.01% to about 0.2% by weight based on 100% of polymeric material.

12. A flameproof formulation according to claim 10, wherein the flow promoter is 2,3-dimethyl-2,3-diphenylbutane.

13. A flameproof formulation according to claim 5, wherein said formulation is injection molded or compression molded.

14. A process for preparing a polybrominated bisaryl compound containing bromomethyl/bromomethylene groups according to formula (I):

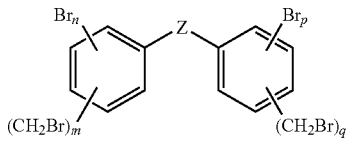
(I)

wherein Z is a bond, —O—, —CH$_2$—, —CH(CH$_3$)—, —OCH$_2$CH$_2$O—, n=1-4, p=1-4, m=1-4, and q=1-4, said process comprising aromatic ring-bromination, followed by benzylic bromination.

15. A process according to claim 14, wherein said bromomethyl bisaryl compound has a formula selected from the group consisting of formulae A to E:

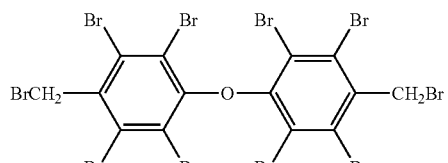
A.

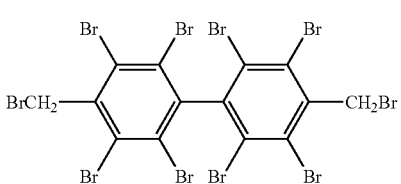
B.

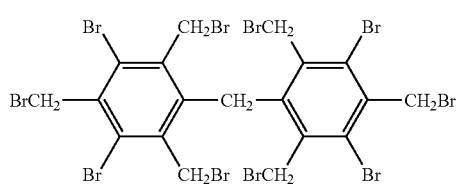
C.

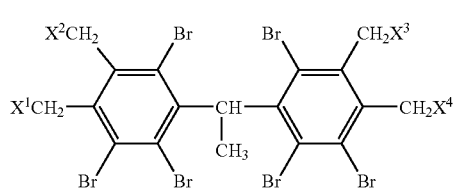
D.

wherein $X^1$, $X^2$, $X^3$, and $X^4$ are independently H or Br wherein at least one of them is Br;

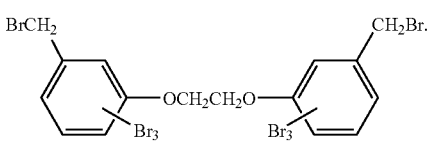
E.

16. A process for preparing a polybrominated bisaryl compound having formula F

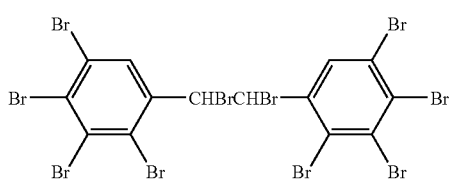
F.

said process comprising bromine addition to the double bond of stilbene, and aromatic ring-bromination.

17. A polybrominated compound according to claim 1, exhibiting a weight loss of up to 10% at 270° C.

18. A flameproof formulation according to claim 8, being essentially transparent.

* * * * *